(12) United States Patent
Geroni et al.

(10) Patent No.: US 8,940,334 B2
(45) Date of Patent: Jan. 27, 2015

(54) PHARMACEUTICAL COMPOSITION OF AN ANTHRACYCLINE

(75) Inventors: Maria Cristina Geroni, Milan (IT); Olga Valota, Legnano (IT); Alessandro Martini, Milan (IT); Paolo Elia Cappella, Saronno (IT)

(73) Assignee: Nerviano Medical Sciences S.R.L., Nerviano (MI) (IT)

(*) Notice: Subject to any disclaimer, the term of this patent is extended or adjusted under 35 U.S.C. 154(b) by 1474 days.

(21) Appl. No.: 12/599,331

(22) PCT Filed: Apr. 30, 2008
(Under 37 CFR 1.47)

(86) PCT No.: PCT/EP2008/055299
§ 371 (c)(1),
(2), (4) Date: Jan. 26, 2012

(87) PCT Pub. No.: WO2008/138758
PCT Pub. Date: Nov. 20, 2008

(65) Prior Publication Data
US 2012/0121716 A1   May 17, 2012

(30) Foreign Application Priority Data
May 11, 2007   (EP) .................................... 07107979

(51) Int. Cl.
| A61K 9/14 | (2006.01) |
| A61K 31/706 | (2006.01) |
| A61K 9/16 | (2006.01) |
| A61K 9/50 | (2006.01) |
| A61K 9/00 | (2006.01) |
| A61K 31/535 | (2006.01) |
| A61K 31/704 | (2006.01) |

(52) U.S. Cl.
CPC ............. *A61K 9/0019* (2013.01); *A61K 31/535* (2013.01); *A61K 31/704* (2013.01)
USPC ............... 424/491; 424/422; 514/34; 514/6.4

(58) Field of Classification Search
CPC . A61K 31/70; A61K 31/7032; A61K 31/519; A61K 9/16; A61K 9/1629; A61K 9/1635; A61K 9/1647; A61K 9/1658; A61K 9/167; C07H 15/24; C07H 471/04
See application file for complete search history.

(56) References Cited

U.S. PATENT DOCUMENTS

| 4,672,057 A | 6/1987 | Bargiotti et al. |
| 5,304,687 A | 4/1994 | Bargiotti et al. |

FOREIGN PATENT DOCUMENTS

| CN | 1824319 A | 8/2006 |
| CN | 1846686 A | 10/2006 |

(Continued)

OTHER PUBLICATIONS

Pacciarini M.A. et al., "Phase I/II Trial of Nemorubicin Hydrochloride in Combination With Cisplatin is Supported by New Preclinical Evidences of its Mechanism of Action", *ASCO Annual Meeting Proceedings Part Part I, vol. 24(18S)*:14116 (2006).

(Continued)

*Primary Examiner* — Lakshmi Channavajjala
(74) *Attorney, Agent, or Firm* — Scully, Scott, Murphy & Presser, P.C.

(57) ABSTRACT

The present invention relates to pharmaceutical composition containing nemorubicin hydrochloride incorporated in microspheres. The compositions are useful for chemoembolization, particularly for loco regional treatment of tumors.

2 Claims, 2 Drawing Sheets

(56) References Cited

FOREIGN PATENT DOCUMENTS

| | | |
|---|---|---|
| CN | 1857723 A | 11/2006 |
| CN | 1923284 A | 3/2007 |
| CN | 101011341 A | 8/2007 |
| WO | WO 00/15203 | 3/2000 |
| WO | WO 00/66093 | 11/2000 |
| WO | WO 2004/071495 A1 | 8/2004 |
| WO | WO 2004/075904 A1 | 9/2004 |
| WO | WO 2004/082579 A2 | 9/2004 |
| WO | WO 2005/087193 A2 | 9/2005 |
| WO | WO 2006/119968 A2 | 11/2006 |

OTHER PUBLICATIONS

Aoki T. et al., "Sequential Preoperative Arterial and Portal Venous Embolizations in Patients With Hepatocellular Carcinoma", *Arch Surg* 139(7):766-774 (Jul. 2004).

Bruix J. et al., "Chemoembolization for Hepatocellular Carcinoma", *Gastroenterology* 127:S179-S188 (2004).

Geschwind J-F H., "Chemoembolization for Hepatocellular Carcinoma: Where Does the Truth Lie?", *J. Vasc. Interv. Radiol.* 13(10):991-994 (Oct. 2002).

Vogl T.J. et al., "Treatment of Unresectable Lung Metastases With Transpulmonary Chemoembolization: Preliminary Experience", *Radiology* 234:917-922 (2005).

Constantin M. et al., "Preparation and Characterisation of Poly(Vinyl Alcohol)/Cyclodextrin Microspheres Matrix for Inclusion and Separation of Drugs", *International Journal of Pharmaceutics* 285(1-2):87-96 (2004).

Lewis A.L. et al., "DC Bead: In Vitro Characterization of a Drug-Delivery Device for Transarterial Chemoembolization", *J. Vasc. Interv. Radiol.* 17:335-342 (2006).

Vallée J-N et al., "In Vitro Study of the Compatibility of Tris-Acryl Gelatin Microspheres With Various Chemotherapeutic Agents", *J. Vasc. Interv. Radiol* 14:621-628 (2003).

Osuga K. et al., "Transarterial Embolization for Large Hepatocellular Carcinoma With Use of Superabsorb Polymer Microspheres: Initial Experience", *J. Vasc. Interv. Radiol.* 13:929-934 (2002).

PHARMACEUTICAL COMPOSITION OF AN ANTHRACYCLINE

SUMMARY OF THE INVENTION

The present invention pertains to the field of neoplastic disease therapy. In particular, the present invention relates to a pharmaceutical composition containing nemorubicin hydrochloride bound to microspheres, to a kit containing nemorubicin hydrochloride and microspheres and to a therapeutic method for loco regional treatment of tumor lesions using such pharmaceutical composition.

BACKGROUND OF THE INVENTION

Nemorubicin hydrochloride, chemical names (8S-cis, 2"S)-7,8,9,10-tetrahydro-6,8,11-trihydroxy-8-(hydroxyacetyl)-1-methoxy-10-{[2,3,6-trideoxy-3-(2-methoxy-4-morpholinyl)-α-L-lyxo-hexopyranosyl]oxy}-5,12-naphthacenedione hydrochloride and 3'desamino-3'[2(S)methoxy-4-morpholinyl]doxorubicin-hydrochloride (below referred to as nemorubicin hydrochloride only) of formula

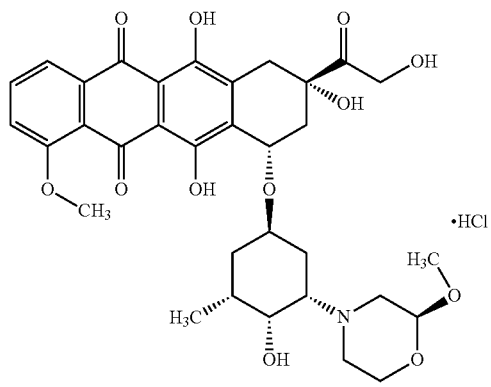 [SMILES: COc1cccc2c1C(=O)c1c(O)c3c(c(O)c1C2=O)C[C@@](O)(C(=O)CO)C[C@@H]3O[C@@H]1C[C@@H](C)[C@@H](O)[C@@H](N2CCO[C@H](OC)C2)C1 ; Cl]

is a doxorubicin derivative obtained with the substitution of the —NH$_2$ at position 3° in the sugar moiety with a methoxymorpholino group. The compound was synthesized in the course of a research program aimed at identifying new anthracyclines with at least partially novel modes of action, and possessing broad spectrum of activity, including activity on multidrug resistant tumors and lower toxicity than doxorubicin as far as cardiotoxicity is concerned. U.S. Pat. No. 4,672,057 discloses and claims nemorubicin hydrochloride, preparation process, pharmaceutical compositions and medical uses thereof.

According to WO 00/15203, nemorubicin hydrochloride can be administered via the hepatic artery, for example, as an infusion of from about 15 min to about 30 min every 4 weeks or preferably, as a 5-10 min bolus every 4-8 weeks, to adult patients with either a hepatic metastatic cancer, for example, patients with colorectal cancer who have progressed after receiving intravenous chemotherapy or intrahepatic 5-fluorouracil or 5-fluorodeoxyuridine (FUDR) chemotherapy, or patients with primary liver carcinoma such as, for example, hepatocellular carcinoma or cholangiocarcinoma involving the liver. According to WO 00/15203, nemorubicin hydrochloride can be administered to a patient in a dosage ranging from, e.g., about 100 mcg/m$^2$ to about 1000 mcg/m$^2$, preferably from about 100 mcg/m$^2$ to about 800 mcg/m$^2$, for example, in a dosage of about 200 mcg/m$^2$.

WO 04/75904 describes and claims the use of nemorubicin hydrochloride for the preparation of a medicament for the treatment of a human liver tumor, which comprises intrahepatic administration of nemorubicin hydrochloride via the hepatic artery in a dosage ranging from, e.g., about 100 mcg/m$^2$ to about 800 mcg/m$^2$, preferably from about 200 mcg/m$^2$ to about 600 mcg/m$^2$, for example in a dosage of about 200, 400 or 600 mcg/m$^2$ every 6 weeks.

Two administration schedules have been evaluated in Phase I setting: in one trial nemorubicin hydrochloride was administered by intra-hepatic artery (IHA) as a 30-min infusion every 4 weeks in saline; in another trial, nemorubicin hydrochloride was administered by IHA with iodinated oil as a 5 to 10 min infusion every 6-8 weeks. As described in WO 04/082579 and WO 00/066093, nemorubicin hydrochloride is indicated as a component of therapy in combination with radiotherapy, an alkylating agent, an antimetabolite, a topoisomerase I/II inhibitor or a platinum derivative. Suarato, A et al., ACS Symposium Series (1995), 574 (Anthracycline Antibiotics), pages 142-55 and U.S. Pat. No. 5,304,687 disclose key intermediates and processes for an improved synthesis of nemorubicin hydrochloride.

CN 101011341 and CN 1923284 (Jinan Kangquan Pharmaceutical Science and Technology Co., Ltd.) disclose slow release injections, which comprise microspheres or microballoons that consist of anti-cancer active ingredients and slow-releasing adjuvants and dissolvents.

Nemorubicin Hydrochloride Antitumor Activity

Nemorubicin hydrochloride is a DNA-intercalator, different from classical anthracyclines, in that it works primarily through topoisomerase I as demonstrated by the dominant DNA lesions produced being single strand DNA breaks. The compound shows efficacy on tumors resistant to different anticancer drugs such as platinum derivatives, alkylating agents, topoisomerase I and II inhibitors, taxanes, anthracyclines and vinca alkaloids. In addition, unlike alkylating agents and platinum derivatives, it is effective on cells with upregulation of the nucleotide excision repair pathway or with mismatch repair deficiency.

Nemorubicin hydrochloride was selected for clinical evaluation based on its broad spectrum of activity in experimental models and lower cardiotoxicity than doxorubicin at equally myelotoxic doses in animals.

When nemorubicin hydrochloride was administered intravenously (IV) as single agent to patients, in Phase I-II clinical study setting, anticancer activity was observed in head & neck, cervix and colorectal cancer (in Phase I studies). In Phase I B studies, partial responses (PRs) were reported in non-small-cell-lung cancer, renal cancer and cancer of unknown origin. Regressions were repeatedly reported in liver lesions from primary colorectal and renal cancer. In a Phase II study in sarcomas, 2 PRs were reported out of 26 patients that could be taken into account. In the Phase II investigations in breast cancer patients with liver metastases, 4 objective responses out of 7 treated patients were observed overall. The level of antitumor activity achieved in this study was strongly indicative of the efficacy of nemorubicin hydrochloride in liver lesions and supported further investigation in primary and secondary liver cancer.

Clinical Studies as Single Agent by Intra-Hepatic Artery (IHA) Route

The findings of efficacy in liver lesions reported in the Phase I-II studies by the IV route, coupled with evidence of antitumor efficacy in liver in preclinical models, provided the rationale for specific investigation in hepatocellular carcinoma (HCC). The loco regional approach was chosen in order to decrease the systemic toxicity reported after IV administration.

One Phase I study with saline as a vehicle was conducted by IHA in Europe in patients with HCC and with liver metastases from other solid primary tumors. In addition, one Phase I/II study and one Phase II/III randomized study by IHA route, both with iodinated oil (Lipiodol®) as vehicle, were performed in China in patients with unresectable HCC (Pacciarini, M A et al., Journal of Clinical Oncology, 2006 ASCO Annual Meeting Proceedings Part I. Vol 24, No. 18S, 2006: 14116).

Overall, considering the collective clinical experience gained with nemorubicin hydrochloride administered by IHA route (with and without iodinated oil) to patients with HCC, in Europe and China, 57 HCC patients were taken into account for efficacy. Focusing on perfused liver lesions, there were overall 11/57 confirmed CR/PRs (i.e. a RR of 19.3%, 95% c.i. 10.0-31.9%) lasting from 1 to 54+ months. Disease stabilizations lasting ≥3 months (median duration 4.5 months, range 3-12.5) were reported in 17/57 patients, most of whom had advanced stages of the disease (AJCC Stage III, IIIA and IVA). As far as safety is concerned, nemorubicin hydrochloride showed a manageable safety profile in terms of hematological and hepatic toxicity, as well as nausea and vomiting. The good tolerability and the level of antitumor activity achieved in these studies was strongly supportive of the use of nemorubicin hydrochloride by loco regional approach for the treatment of tumor lesions.

Chemoembolization

In the field of loco regional therapies chemoembolization is a minimally invasive approach for palliative treatment of unresectable tumors. The tumors referred to are primary or metastasis cancers, sarcoma or carcinosarcoma found in brain, central nervous system, kidneys, liver, gall bladders, head and neck, oral cavity, thyroid, skin, mucous membranes, glandular organs, blood vessels, bone tissues, lymph nodes, lungs, esophagus, stomach, lacteal glands, pancreas, eyes, nasopharynge, womb, ovaries, endometrium, cervix, prostate gland, bladders, colon and rectum.

Chemoembolization is also employed as an adjunctive therapy to liver resection or as a bridge to liver transplantation, as well as prior to radiofrequency ablation (Aoki, T et al., Arch Surg. 2004 July; 139(7):766-74; Bruix, J et al. Gastroenterology. 2004 November; 127:S179-88). Chemoembolization has become one of the most commonly performed procedures in interventional radiology.

Chemoembolization typically involves the injection of chemotherapeutic agents, with or without lipiodol and/or embolic agents, into the blood vessels supplying the tumor, e.g. into the branch of the hepatic artery that feeds the tumor lesions at liver level (Geschwind, J. Vasc Intery Radiol. 2002; 13(10):991-4), into the right or left pulmonary artery that feeds the tumor lesions at lung level (Vogl T J. et al. Radiology 2005; 234:917-22). The embolic agents keep the chemotherapeutic agent in the tumor by blocking the flow to other areas of the body.

Currently, there is intense research activity in the area of nanotechnology and drug-delivery systems. The ideal drug-loaded carriers should deliver the agent precisely, release it in a controlled and sustained manner and achieve high intra-tumor drug concentration for a sufficient period, without damaging the surrounding normal tissue. Several drug-delivery systems for loco regional treatment of tumors, such as microspheres, have been recently tested (Constantin, M et al., Int J Pharm. 2004 Nov. 5; 285(1-2):87-96). Microspheres are essentially solid porous particles (50-1200 micrometer diameter), which can both target their drug cargo by physical trapping in blood vessels (chemoembolization) and sustain the action of a therapeutic agent through controlled release.

Microspheres can be made from a broad range of polymeric materials, such as polyvinyl alcohol (PVA), 2-acrylamido-2-methyl-1-1-propane-sulphonoc acid (AMPS), poly (lactide-co-glycolide) (FLOG).

In WO2004/071495 and WO2005/087193, microspheres are loaded with a single chemotherapeutic agent, such as doxorubicin, and infused intra-arterially for selective tumor targeting.

Sulphonate-modified N-Fil hydrogel microspheres (polyvinyl alcohol), trade name DC Bead™ (Biocompatibles) microspheres and so referred to herein below, are described as capable of loading doxorubicin in an article of Lewis et al (J. Vasc. Interv. Radiology; 2006; 17-335-442).

Trisacrylgelatin collagen-coated microspheres, trade name Embosphere® microspheres (BioSphere Medical), and expanding microspheres, trade name HepaSphere™ (BioSphere Medical), so referred to herein below, are described as capable of loading anticancer agents (Vallée J N et al. J Vasc Intery Radiol 2003; 14:621-8; Osuga K. et al. JVIR 2002; 13:929-34).

The critical determinants in defining the pharmacological activity of chemoembolization performed with microspheres are represented by:

preservation of the native conformation of the microspheres (in terms of size, spherical shape and plasticity), to guarantee the appropriate occlusion of the lumen of the vessel, avoiding distal embolization.

loading rate of the chemotherapeutic agents into the microspheres, to guarantee the administration of a therapeutic dose.

release rate of the chemotherapeutic agents from the microspheres, to guarantee the availability of the chemotherapeutic agents in a sustained manner and the achievement of high intra-tumor drug concentration for a sufficient period of time, without damaging the surrounding normal tissue.

kinetics of release of the chemotherapeutic agents from the microspheres, to guarantee a prolonged and complete release of the chemotherapeutic agents.

use of an appropriate amount of microspheres to guarantee the administration of an accurate dose of chemotherapeutic agent.

The active drug substance incorporated in the system usually influences significantly the clinical performances of the microspheres by altering or modifying their physico-chemical parameters, such as, as example the particle size distribution, thus impacting on the expected occlusion of the lumen of the vessel, avoiding distal embolization (i.e. if the microsphere is shrunk by the presence of the drug, the risks of distal embolization are higher), the release kinetic of the active drug substance from the formulation and drug stability.

We have surprisingly found a way of overcoming all such drawbacks.

BRIEF DESCRIPTION OF THE DRAWING

The invention is also illustrated by reference to the accompanying drawings described below.

Pictures coded A, D and G are controls, microspheres with no drug;

pictures coded B, E and H show nemorubicin hydrochloride loaded microspheres, 1 mg/ml and pictures coded C, F and I show doxorubicin loaded microspheres, 25 mg/ml.

Figure 2:
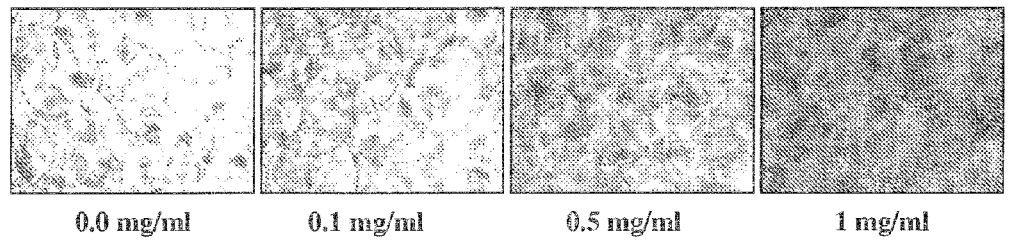

FIG. 2 shows microscope examinations of DC Bead™ microspheres suspension prepared in Example 2, after 1 h loading of different amounts of nemorubicin hydrochloride (no drug, 0.1, 0.5 and 1 mg/ml).

Figure 3:
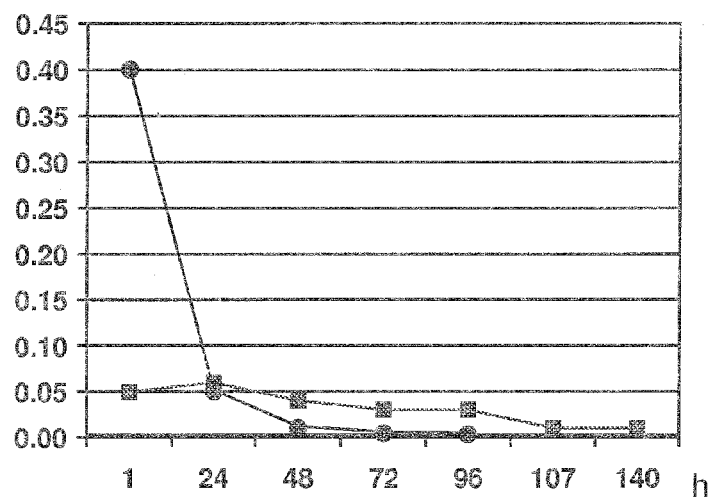

FIG. 3 shows the graph obtained from HPLC/MS analysis of kinetic of release of nemorubicin hydrochloride and doxorubicin from DC Bead™ microspheres prepared in Example 3, that were respectively loaded with 1 mg nemorubicin hydrochloride/ml DC Bead™ microspheres or 1 mg doxorubicin/ml DC Bead™ microspheres in phosphate buffer saline solution (PBS). On the Y axis are indicated the amounts of eluted nemorubicin hydrochloride (●) and doxorubicin (■) in mg of drug/ml of DC Bead™ microspheres, on the X axis the elution times in hours.

Figure 4:
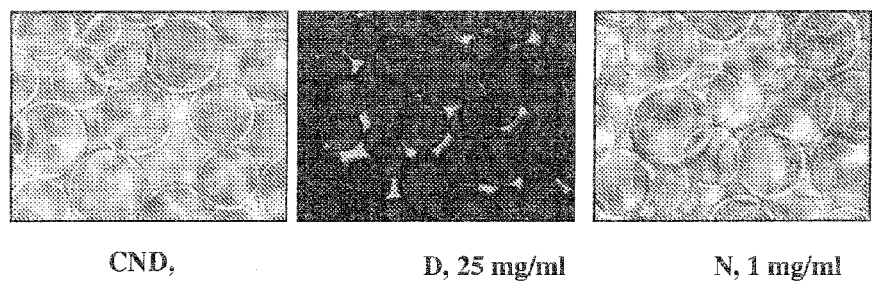

FIG. 4 shows microscope examinations of DC Bead™ microspheres suspension 16 days after nemorubicin hydrochloride (N) or doxorubicin (D) release; CND control no drug.

DETAILED DESCRIPTION OF THE INVENTION

The first object of the present invention is a composition comprising nemorubicin hydrochloride incorporated in a microsphere system.

Preferably, nemorubicin hydrochloride is incorporated in the microsphere system without adding any releasing adjuvant.

It is to be noted that there are no physico-chemical changes of the microspheres loaded with nemorubicin hydrochloride, thus allowing a more reproducible and safer administration of the drug than the ones achievable with other oncologic active drug substances foreseen for the use. Suitable microspheres for the present invention, as stated before, can be made from a broad range of polymeric materials, such as polyvinyl alcohol (PVA) 2-acrylamido-2-methyl-1-1-propane-sulphonoc acid (AMPS), poly(lactide-co-glycolide) (PLCG) or trisacrylgelatin having a coating of collagen. Methods for their preparation are described for example in WO2004/071495, WO2005/087193 and WO2206/119968.

Preferably, the microspheres of the present invention are made of water-swellable, water insoluble polymer. In particular, the present invention mainly relates to sulphonate-modified N-Fil hydrogel microspheres as preferred carrier on which loading nemorubicin hydrochloride.

Therefore, a preferred composition according to the present invention comprises nemorubicin hydrochloride loaded on sulphonate-modified N-Fil hydrogel microspheres. Such microspheres can be prepared as described in the above cited article of Lewis et al.

Preferably, nemorubicin hydrochloride is loaded in a concentration range of from 0.1 to 10 mg drug/ml of microspheres. Such loading can be carried out in a reproducible manner both in terms of loading and of release kinetic of nemorubicin hydrochloride from the formulation itself.

What has been surprisingly found is that, by making sizing analysis at microscope by means of an image analysis technique, the microspheres loaded with nemorubicin hydrochloride have unique features with respect to what is known in the prior art. As a matter of fact, the microspheres not only maintain their spherical shape, but also keep the original size as unloaded. No aggregation is observed as for unloaded microspheres. These characteristics are maintained for all the expected release time of the formulation that can last from few h to about 15 days.

All the above features are not only unexpected, but offer a great advantage for the administration of the nemorubicin hydrochloride formulation in microspheres versus other drugs in terms of easiness, reproducibility and quantitative results as far as the loading process is concerned; in terms of reproducible and predictable release profiles from the loaded spheres (i.e. being the releasing surface constant, the release kinetic of the active from the formulation can be predicted easily); and more reproducible administration and control of the formulation along the clinical setting.

No needs of recalculation of the quantity and volume of microspheres to be administered to patients is needed while administering the nemorubicin hydrochloride/microspheres system, nor any manipulation along the administration practice that is necessary for other drug/microspheres system being the material shrunk by the presence of the active drug substance and being needed the use of empirical calculation to predict in advance the impact of the shrinkage of the formulation to the quantity of beads and the size of beads to be administered to obtain the proper embolization.

These unique features of the nemorubicin hydrochloride/microspheres loaded formulation are evident when the data herein are compared to the one described in the literature article of Lewis et al cited above, where the loading of doxorubicin (a drug of the same chemical class of anthracyclines as nemorubicin hydrochloride is) in the DCBead™ microspheres not only is dose dependant (i.e. loading time and efficiency vary according to the drug to bead ratio), but also induce a severe shrinkage of the DCBead™ microspheres and influence the release rate kinetic of the drug itself from the delivery system both in vitro and in vivo.

In addition, the extended antitumor effect of nemorubicin hydrochloride while administered by means of the microspheres was surprising, being the active drug substance chemically stable only up to 24 h at room temperature and being its degradation products inactive as far as cytotoxicity and antitumor efficacy is concerned. It is evident that the nemorubicin hydrochloride/microspheres formulation was more chemically stable than the active drug substance per se while administered as loco regional therapy and that the microspheres system exerts a protective effect towards the chemical stability of nemorubicin hydrochloride, thus allowing the release in a controlled and sustained matter exclusively of the active moiety.

The pharmaceutical composition containing nemorubicin hydrochloride bound to microspheres allows a release rate of nemorubicin hydrochloride from the microspheres able to guarantee the availability of nemorubicin hydrochloride in a sustained manner and the achievement of a drug concentration able to kill tumor cells.

In addition, the kinetics of release of nemorubicin hydrochloride from microspheres guarantees a prolonged and high release rate of nemorubicin hydrochloride.

Nemorubicin hydrochloride loading, at all clinically useful concentrations, resulted in an unchanged average size of the microspheres. This allows an accurate embolization of tumor vessels. Conversely, commercial microspheres loaded with doxorubicin have a decrease in the average size; this can impact the accuracy of the drug release in the targeted region, can reduce the efficacy against tumor, and may increase the risk of complications.

In particular, the composition containing nemorubicin hydrochloride bound to microspheres preserves the native conformation of the microspheres (in terms of size, spherical shape and plasticity) and guarantees the appropriate occlusion of the lumen of the vessel, avoiding distal embolization.

In summary, microspheres can be easily loaded with nemorubicin hydrochloride at clinically useful dosages. Nemorubicin hydrochloride-microspheres loading and elution data support considering nemorubicin hydrochloride a suitable drug for chemoembolization through microspheres.

Loading of efficacious clinical quantity of nemorubicin hydrochloride on the microspheres has been tested in the range between 0.1 and 10 mg drug/ml of microspheres and happens in such reproducible way that the same loading procedure and standard loading time could be applied independently from the drug concentration in the loading vehicle. Also this feature offers an unique advantage in terms of deliverability of the system, granting not only a precise, accurate and reproducible titration of the drug in the clinical setting, but also a more accurate and reproducible embolization.

The microspheres loaded with nemorubicin hydrochloride are a safer chemoembolization treatment in comparison with known ones. In fact, other commercial microspheres loaded for example with doxorubicin remain loaded with high levels of drug for several days and, due to the severe shrinkage of the microspheres loaded with doxorubicin, doxorubicin can be released far from the tumor area increasing its adverse effects.

The present invention provides also a method of treating patients suffering from a cancer. In particular, the present invention offers a method of treating patients suffering tumors for which a loco regional approach is feasible, such as primary or metastasis cancers, sarcoma or carcinosarcoma found in brain, central nervous system, kidneys, liver, gall bladders, head and neck, oral cavity, thyroid, skin, mucous membranes, glandular organs, blood vessels, bone tissues, lymph nodes, lungs, esophagus, stomach, lacteal glands, pancreas, eyes, nasopharynge, womb, ovaries, endometrium, cervix, prostate gland, bladders, colon and rectum.

More preferably the present invention provides method of treating patients suffering liver tumor (i.e., hepatocellular carcinoma or cholangiocarcinoma or liver metastases).

The composition which is administered to a patient in need of embolotherapy having a tumor, for instance a hepatocellular carcinoma, is an aqueous suspension of swollen particles containing the drug. It is often desirable for the suspension to be mixed prior to delivery with an imaging agent such as a conventional radio-opaque agent, as is used for gel type embolic compositions.

Nemorubicin hydrochloride is administered in a dosage ranging from e.g. about 0.1 to 10 mg/m². More preferably, the course therapy employed is from 0.1 to 5 mg/m².

The pharmaceutical composition containing nemorubicin hydrochloride bound to microspheres allowed a fast loading (about 1-2 h incubation) and a loading rate of nemorubicin hydrochloride into the microspheres (>99%) able to guarantee an easy administration of therapeutic doses of nemorubicin hydrochloride to patients.

In a still more particular embodiment of the present invention, the appropriate dose of nemorubicin hydrochloride, preferably previously dissolved in adequate solution, is mixed with a suitable amount of microspheres.

It is a further object of the invention a product or kit comprising nemorubicin hydrochloride and microspheres for use in the preparation of a medicament for the loco regional treatment of a cancer.

The selection of the size of the microspheres is based on the vascular target/vessel size. The following table illustrates the available microsphere size ranges:

| Microspheres size |
|---|
| 50-100 μm |
| 100-300 μm |
| 300-500 μm |
| 500-700 μm |
| 700-900 μm |
| 900-1200 μm |

The reconstituted nemorubicin hydrochloride solution must be added to the microspheres and agitated gently to encourage mixing.

Loading will take a minimum of 20 minutes for the smallest size microspheres up to 3 h for the largest size microspheres.

The delivery catheter must be introduced into the target vessel according to standard interventional radiology technique for chemoembolization. The embolization must be monitored under fluoroscopic visualization by adding the desired amount of contrast medium (such as a conventional radio-opaque agent as is used for gel type embolic composition) to the suspension fluid, for instance in amounts in the range 1:5 to 2:1, preferably in the range 1:2 to 1:1 by volume.

Nemorubicin hydrochloride-microspheres must be slowly injected into the delivery catheter under fluoroscopic visualization while observing the contrast flow rate.

Upon completion of the treatment, the catheter must be removed while maintaining gentle suction so as not to dislodge microspheres still within the catheter lumen.

The embolic composition as administered to the patient in need of embolization therapy, may be delivered as a single one-off dosage. Embolization is monitored by following the contrast agent using conventional techniques. It may be found to be desirable for subsequent doses of an embolic composition useful in the invention, to be delivered at a time interval after the previous dose, for instance to embolise newly formed blood vessels supplying the tumor e.g. after 4 to 10 weeks from the previous treatment for a nemorubicin hydrochloride—containing composition.

The present invention is illustrated in the following examples.

EXAMPLE 1

Evaluation of Size and Spherical Shape of DC Bead™ Microspheres in the Pharmaceutical Composition Containing Nemorubicin Hydrochloride DC Bead™ Microspheres—Sizing and Appearance Nemorubicin hydrochloride was diluted at the concentration range of from 0.1 to 2.0 mg drug/ml DC Bead™ that represent clinically applicable doses. In the following examples microspheres of 100-300 μm diameters (DC Bead™) were used. Similar results were obtained when microspheres of 300-500 μm diameters (DC Bead™) were used.

The size and spherical shape of microspheres were analyzed after loading with nemorubicin hydrochloride and during the release of the drug up to 16 days. As comparison DC Bead™ microspheres were loaded with doxorubicin at the clinically used dosage of 25 mg drug/ml DC Bead™.

Drug loading: DC Bead™ microspheres were conditioned in water for 10 min. Then the water was discarded and nemorubicin hydrochloride or doxorubicin was added.

Drug release: DC™ microspheres with or without drug were incubated in Phosphate Buffer Saline (PBS) or human plasma from healthy donors up to 16 days. The size and spherical shape of DC Bead™ microspheres were measured at different time points.

Size and appearance of nemorubicin hydrochloride-DC Bead™ microspheres during drug-loading and drug-elution were determined by a Leica DM IRB (Leica) microscope equipped by Evolution MP Color CCD Camera (Media Cybernatics). The analysis of size was performed by Image Pro Plus™ (Media Cybernatics). 108 µm-reference beads (PMMA 90-125 µm, Bangs Laboratories, Fisher, Ind.) were used for size calibration. At least four field-images for samples were analyzed to support the statistical analysis.

Results

Figure 1:
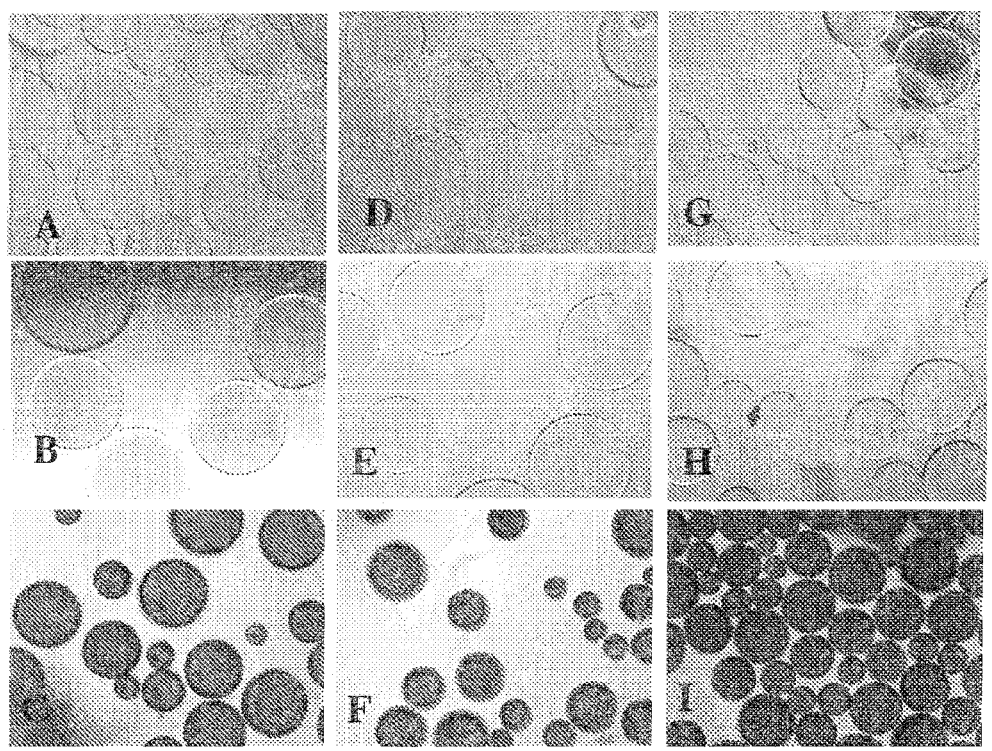
FIG. 1 shows microscope examinations of DC Bead™ microspheres (100-300 μm size), suspension prepared in Example 1 at 1 h loading (pictures A, B and C), after elution at one day (pictures D, E and F) and after elution at day 7 (pictures G, H and I) in phosphate buffer saline solution (PBS).

As reported in Table 1 and FIG. 1, what was surprisingly found was that, by making sizing analysis at microscope by means of an image analysis technique, the loaded DC Bead™ microspheres had unique features with respect to what is known in the prior art. In fact, they not only maintained their spherical shape, but also kept the original size as unloaded both after drug loading and drug release. No aggregation was observed as for unloaded DC Bead™ microspheres. These characteristics were maintained for all the observation period up to 16 days.

TABLE 1

Size of DC Bead ™ microspheres after drug-loading and at different drug-elution times in PBS (diameter evaluation by image analysis at microscope).

|  | Time (h) | Control Microspheres + PBS | | Microspheres + Nemorubicin hydrochloride 1 mg drug/ml DC Bead ™ | | Microspheres + Doxorubicin 25 mg drug/ml DC Bead ™ | |
|---|---|---|---|---|---|---|---|
|  |  | Mean (Ø µm) | CV % | Mean (Ø µm) | CV % | Mean (Ø µm) | CV % |
| Loading | 1 | 254 | 19 | 299 | 14 | 85 | 31 |
| Elution | 1 | 266 | 19 | 258 | 25 | 94 | 32 |
|  | 24 | 286 | 24 | 291 | 22 | 98 | 28 |
|  | 48 | 271 | 18 | 251 | 16 | 107 | 33 |
|  | 72 | 260 | 14 | 230 | 24 | 122 | 27 |
|  | 96 | 250 | 13 | 221 | 19 | 125 | 34 |

As shown in Table 1 and FIG. 1, the loading of nemorubicin hydrochloride provided size and aspect as unloaded microspheres diameter (size range 250-286 µm for control and 230-291 µm for nemorubicin). Conversely, doxorubicin showed reduced size (size range 85-125 µm for doxorubicin) and great heterogeneity (increased CV %, coefficient of variation %).

As shown in FIG. 1, the above results support the administration of the nemorubicin hydrochloride formulation on DC Bead™ microspheres advantageous versus other drugs in terms of easiness and more reproducible administration and control of the formulation along the clinical setting.

EXAMPLE 2

Loading of DC Bead™ Microspheres with Nemorubicin Hydrochloride

DC Bead™ microspheres were loaded with the active drug substance by means of a standard protocol applied also in the clinical setting. The packing solution was removed from the microspheres. Subsequently, DC Bead™ microspheres were conditioned one time by water and required volume of nemorubicin hydrochloride solution was added to DC Bead™ microspheres. The dose of nemorubicin hydrochloride used for this experimental study was 0.5 and 2 mg drug/ml DC Bead™ microspheres. Added drug loading volumes were in agreement with the prior art and with what is compliance to described in DC Bead™ microspheres guide-lines.

The mixture was roller-mixed gently and kept at 37° C. for different period of time, up to 2 h. At the end of loading time, nemorubicin hydrochloride-DC Bead™ microspheres were washed by water and all fractions were collected for nemorubicin hydrochloride quantification. The loading of nemorubicin hydrochloride was calculated by measuring the remaining drug concentration in solution over time.

The measurements of nemorubicin hydrochloride in the elution medium were carried out with HPLC-MS/UV analysis performed by Finnigan MAT/LCQ Deca XP ion trap MS equipped with ESI ion source, directly connected to a Surveyor HPLC system (Thermo Electron Corporation). HPLC-MS/UV separations were set up on Phenomenex Gemini Phenyl, 3 µm, 50×4.6 mm by Acetate Buffer:Acetonitrile 1:9. UV detection was done at 480 nm and for ESI-MS analysis a heated capillary temperature at 275° C. and spray voltage at 4 KV was applied.

The measurements were carried out with HPLC-MS/UV analysis versus a standard curve of nemorubicin hydrochloride. The loading efficiency was calculated substantially as below:

Loading Efficiency(%)=100×(Initial drug amount−residual founded drug)/Initial drug amount.

Results

The loading efficiency of nemorubicin hydrochloride to DC Bead™ microspheres was more than 99% up to 2 mg drug/ml DC Bead™ microspheres in non-ionic solution (water). DC Bead™ microspheres analysis at microscope showed that the loading kinetic is very quick, dose-dependent, and always complete up to more than 99% (see Table 2 and FIG. 2).

TABLE 2

Loading efficiency of DC Bead ™ microspheres(100-300 µm size) exposed to different concentrations of nemorubicin

|  | Time of incubation | | |
|---|---|---|---|
|  | 1 h | 2 h | 1 h |
| Drug in the incubation medium (water) | Nemorubicin hydrochloride 1 mg drug/ml microspheres | Nemorubicin hydrochloride 1 mg drug/ml microspheres | Nemorubicin hydrochloride 2 mg drug/ml microspheres |
| % drug loading | 99.8 | 99.6 | 99.8 |

EXAMPLE 3

Release of Nemorubicin Hydrochloride from DC Bead™ Microspheres

The release of nemorubicin hydrochloride from DC Bead™ microspheres was evaluated in PBS and in human plasma. At the end of the loading time and at each elution point, loaded nemorubicin hydrochloride-DC Bead™ microspheres were washed by warm water and finally incubated in warm PBS or human plasma at 37° C.

At desiderate elution time supernatant was collected carefully by syringe, avoiding beads aspiration. Then solutions were filtered by 70 μm nylon filcon filter (BD Biosciences) to avoid carry-over contamination, collected in Eppendorf tubes and finally stored at −20° C. for further analysis.

Doxorubicin was tested in comparison.

Samples were split for:
   evaluation of the cytotoxicity of nemorubicin hydrochloride and doxorubicin against tumor cells (as dose able to inhibit cell growth by 50%; $IC_{50}$).
   evaluation of the released amount of nemorubicin hydrochloride and doxorubicin by HPLC-MS/UV analysis (the method used is reported in Example 2).

In Vitro Antitumor Activity

The cytotoxic effect of elution fractions was investigated on human mammary adenocarcinoma cells (MCF-7, ECACC source). Cells were grown in E-MEM/Glutamax medium (Invitrogen), 10% FBS (EuroClone), and 1% Non-Essential AminoAcids (Invitrogen) and maintained at 37° C. at 5% $CO_2$. For cytotoxicity test, cells were plated at density of 5,000 cells/well in 96-well plates (Corning) and grown for 24 h before treatment. Cells were treated for 72 h by raise dilutions of elution fractions. At the end of treatment, cells were incubated with TS substrate (ATPLite™). Plates were read for chemiluminescence (480/540 nm) by Perkin Elmer Envision™ plate reader.

$IC_{50}$ were calculated by LSW Data Analysis™ curve fitting. The $IC_{50}$ value of nemorubicin hydrochloride and doxorubicin in the medium eluted from DC Bead™ microspheres was compared to that of standard nemorubicin hydrochloride or doxorubicin fresh solutions.

Results

As shown in Table 3, the fractions containing eluted drugs, showed cytotoxic effect comparable to that of nemorubicin hydrochloride or doxorubicin external standard up to 96 h. After this period of time, the solution from nemorubicin hydrochloride-DC Bead™ microspheres or doxorubicin-DC Bead™ microspheres were less cytotoxic.

TABLE 3

Time dependence of $IC_{50}$ values of nemorubicin hydrochloride and doxorubicin eluted from DC Bead ™ microspheres on MCF-7 cancer cells

| | $IC_{50}$ | | | | | | | Standard |
|---|---|---|---|---|---|---|---|---|
| | Time (h) | | | | | | | |
| | 1 | 24 | 48 | 72 | 96 | 120 | 144 | |
| Nemorubicin | 0.045 | 0.035 | 0.048 | 0.043 | 0.066 | >5 | >5 | 0.05 |
| Doxorubicin | 0.3 | 0.25 | 0.18 | 0.14 | 0.20 | 0.45 | 1.5 | 0.25 |

Kinetic of Nemorubicin Hydrochloride Release from DC Bead™ Microspheres in Comparison with Doxorubicin As shown in FIG. 3, the release of nemorubicin hydrochloride was faster than that of doxorubicin. The comparison between nemorubicin hydrochloride and doxorubicin release in PBS showed an half-life value of 1085 h and 1487 h, respectively.

Surprisingly, in human plasma the total drug released from nemorubicin hydrochloride-DC Bead™ microspheres was very high (≥90%). Conversely doxorubicin remained entrapped into microspheres (total drug released 2.5%). These results are fully supported by the analysis at microscope showing that microspheres loaded with nemorubicin hydrochloride were empty after 96 h, conversely microspheres loaded with doxorubicin showed a huge amount of entrapped drug (FIG. 4).

EXAMPLE 4

Release of Nemorubicin Hydrochloride from HepaSphere™ Microspheres (in Comparison with Doxorubicin)

Nemorubicin hydrochloride (1 mg drug/ml HepaSphere™, 2.5 mg drug/ml HepaSphere™) and doxorubicin (1 mg drug/ml HepaSphere™, 2.5 mg drug/ml HepaSphere™, 25 mg drug/ml HepaSphere™) were mixed with HepaSphere™ microspheres (50-100 μm). After 20 minutes of incubation the elution efficiency of nemorubicin hydrochloride and doxorubicin was measured up to 168 h.

At desiderate elution time, supernatant was collected carefully by syringe, avoiding beads aspiration. Then solutions were collected in Eppendorf tubes and stored at −20° C. for further analysis.

The released amount of nemorubicin hydrochloride and doxorubicin was evaluated by HPLC-MS/UV analysis (the method used is reported in Example 2).

As shown in Table 4, the elution efficiency of nemorubicin hydrochloride was higher than that of doxorubicin.

TABLE 4

Elution efficiency of nemorubicin hydrochloride and doxorubicin from HepaSphere ™ microspheres (50-100 μm) up to 168 h.

| Drug | Dose (mg drug/ml HepaSphere ™) | % total released drug |
|---|---|---|
| Nemorubicin | 1 | 86 |
| | 2.5 | 85 |
| Doxorubicin | 1 | 7 |
| | 2.5 | 4 |
| | 25 | 35 |

The invention claimed is:

1. A composition comprising nemorubicin hydrochloride incorporated in a microsphere system without adding any releasing adjuvant, wherein the microspheres are made from polymeric materials selected from the group consisting of sulphonate-modified N-Fil hydrogel polyvinyl alcohol (PVA), wherein the diameter of the microspheres range from 221 μm-291 μm.

2. A composition according to claim 1, in which nemorubicin hydrochloride is loaded/mixed in a concentration range of from 0.1 to 10 mg drug/ml microspheres.

* * * * *